US009226999B2

(12) United States Patent
Nakel et al.

(10) Patent No.: US 9,226,999 B2
(45) Date of Patent: *Jan. 5, 2016

(54) USE OF NONIONIC ESTERS IN A COATING FOR SURFACES COMING IN CONTACT WITH BLOOD

(75) Inventors: Mathias Nakel, Burladingen/Ringingen (DE); Birgit Eisenlohr, Hechingen (DE)

(73) Assignee: MAQUET CARDIOPULMONARY AG, Rastatt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/481,601

(22) Filed: May 25, 2012

(65) Prior Publication Data
US 2012/0238771 A1 Sep. 20, 2012

Related U.S. Application Data

(63) Continuation of application No. 12/028,246, filed on Feb. 8, 2008, now Pat. No. 8,187,622, which is a continuation of application No. PCT/EP2006/007867, filed on Aug. 9, 2006.

(51) Int. Cl.
A61L 33/04 (2006.01)
A61L 33/00 (2006.01)

(52) U.S. Cl.
CPC ............. *A61L 33/04* (2013.01); *A61L 33/0082* (2013.01); *Y10T 428/31507* (2015.04); *Y10T 428/31565* (2015.04); *Y10T 428/31663* (2015.04); *Y10T 428/31786* (2015.04); *Y10T 428/31797* (2015.04)

(58) Field of Classification Search
None
See application file for complete search history.

(56) References Cited

U.S. PATENT DOCUMENTS

| | | | | |
|---|---|---|---|---|
| 3,878,830 A * | 4/1975 | Bicher | | 600/360 |
| 5,162,102 A * | 11/1992 | Nogawa et al. | | 422/48 |
| 5,195,969 A * | 3/1993 | Wang et al. | | 604/96.01 |
| 5,509,899 A | 4/1996 | Fan et al. | | |
| 6,017,493 A | 1/2000 | Cambron et al. | | |
| 6,096,269 A | 8/2000 | Charlton et al. | | |
| 6,176,849 B1 | 1/2001 | Yang et al. | | |
| 6,403,122 B1 * | 6/2002 | Andrysek et al. | | 424/484 |
| 6,506,340 B1 | 1/2003 | Tsai et al. | | |
| 6,610,068 B1 | 8/2003 | Yang | | |

| | | |
|---|---|---|
| 2001/0003796 A1 | 6/2001 | Yang et al. |
| 2002/0019037 A1 | 2/2002 | Caldwell et al. |
| 2012/0238771 A1 | 9/2012 | Nakel et al. |

FOREIGN PATENT DOCUMENTS

| | | |
|---|---|---|
| DE | 10221055 | 11/2003 |
| EP | 0309345 | 9/1988 |
| EP | 0404515 | 6/1990 |
| EP | 0535485 | 4/1993 |
| JP | S-57-159716 A | 10/1982 |
| JP | 2003-500116 | 1/2003 |
| JP | 2003-510134 | 3/2003 |
| JP | 2004-531466 A | 10/2004 |
| WO | WO 86/02933 | 5/1986 |
| WO | WO 00/50106 | 8/2000 |
| WO | WO 01-23015 | 4/2001 |
| WO | WO 01/23015 | 4/2001 |
| WO | WO 03/094991 | 11/2003 |
| WO | WO 2005/004946 | 1/2005 |

OTHER PUBLICATIONS

Cognis, Product Data Sheet, Jun. 2004, pp. 1-2.*
Karl Muller, Untersuchungen uber Cremophor EL, 3 TENSIDE (1966), pp. 37-45.*
David Kessel et al., Fractionation of Cremophor EL Delineates Components Responsible for Plasma Lipoprotein Alterations and Multidrug Resistance Reversal, 7 Oncology Research (1995), pp. 207-212.*
Gelderblom et al., "Cremophor EL: the drawbacks and advantages of vehicle selection for drug formulation," *European Journal of Cancer*, 37: 1590-1598 (2001).
Gelderblom et al., "Cremophor EL: the drawbacks and advantages of vehicle selection for drug formulation," *European Journal of Cancer*, vol. 37, pp. 1590-1598, 2001.
Henneuse-Boxus et al., "Surface Functionalization of PEEK Films Using Photochemical Routes," *European Polymer Journal*, 37: 9-18 (2001).
Higuchi et al., "Serum Protein Adsorption and Platelet Adhesion on Pluronic™ Adsorbed Polysulfone Membranes," *Biomaterials*, 24: 3235-3245 (2003).
Zengil et al., "Effects of polysorbates and Cremophor EL on vascular responses in rat aorta," *Experientia*, vol. 51, pp. 1055-1060, 1995.

(Continued)

*Primary Examiner* — Scott Long
*Assistant Examiner* — Lyndsey Beckhardt
(74) *Attorney, Agent, or Firm* — Grace Doe; Kirk Swenson; Wesley Scott Ashton

(57) ABSTRACT

The present invention relates to methods for coating at least one surface of a medical device for improving the hemocompatibility of said surface. Further, the invention relates to medical devices comprising surfaces, coated with a coating composition containing a nonionic ester formed from an acyclic $C_3$-$C_6(OH)_{3-6}$ polyol and from at least three $C_{12}$-$C_{26}$ fatty acids, and further includes at least one hydrophilic group.

15 Claims, No Drawings

(56) References Cited

OTHER PUBLICATIONS

Trosell, Alejandra I. Lopez, "Effects of Nonionic Surfactants on the Interactions of Different Nanoparticle Materials on Glass Surfaces", Dissertation (The Technical University of Berlin), Mar. 30, 2005, 114 pages.

Stubenrauch, Cosima, et al., "Interactions between Nonpolar Surfaces Coated with the Nonionic Surfactant Hexaoxyethylene Dodecyl Ether C12E6 and the Origin of Surface Charges at the Air/Water Interface", Langmuir, vol. 20, 2004, pp. 4977-4988.

Medical definition of term 'Nonhemolytic', Online Merriam-Webster Dictionary, http://www.merriam-webster.com/medical/nonhemolytic, printed on Apr. 9, 2015, 2 pages.

Medical definition of term 'Hemolytic', Online MedTerms Medical Dictionary, http://www.medicinenet.com/script/main/art.asp?articlekey=15490&pf=2, printed on Apr. 9, 2015, 2 pages.

Lippi, Guiseppe, et al., "Influence of hemolysis on routine clinical chemistry testing", Clin. Chem. Lab. Med., vol. 44, No. 3, 2006, pp. 311-316.

Cardiopulmonary Bypass Machine, at http://www.ebme.co.uldarticles/clinical-engineering/22-cardiopulmonary-bypass— (downloaded Aug. 17, 2015).

R.T. Guest, Castor Oil Hydrogenated, Cellulose Microcrystalline, pp. 128-129, Feb. 11, 2009 (downloaded at http://db.yaozh.com/fuliao6/Castor-Oil-Hydrogenated.pdf).

PEG-40 Hydrogenated Castor Oil, Technical Data Sheet, Cationa Chemical Corporation, CCC. SD.01.07 / REV.00 (downloaded at http://www.cationa.com/docs/Cationa_TDS_PEG-40%20Hydrogenated%20Castor%20Oil.pdf).

Polyoxyl 40 Hydrogenated Castor Oil, Chemidplus—61788-85-0, at http://chem.sis.nlm.nih.gov/chemidplus/rn161788-85-0 (downloaded Aug. 17, 2015).

\* cited by examiner

USE OF NONIONIC ESTERS IN A COATING FOR SURFACES COMING IN CONTACT WITH BLOOD

CROSS-REFERENCES TO RELATED APPLICATIONS

This application is a continuation of U.S. patent application Ser. No. 12/028,246, filed Feb. 8, 2008 now U.S. Pat. No. 8,187,622, which is a continuation of international patent application PCT/EP 2006/007867 filed on Aug. 9, 2006 and designating the U.S., which was published in German as WO/2007/0199940 and claims priority of German patent application DE 10 2005 040 211.9 filed on Aug. 16, 2005. The entire contents of these priority applications are incorporated herein by reference.

BACKGROUND OF THE INVENTION

The present invention relates to the use of at least one nonionic ester in a coating for surfaces which come into contact with blood to improve the hemocompatibility of the surfaces.

The invention further relates to a medical device having at least one surface which has a coating in which a nonionic ester is used.

RELATED PRIOR ART

Various coating compositions and methods for coating medical devices are known in the state of the art.

Plastics surfaces which come into contact with a patient's blood over longer or shorter periods are used in many medical treatments. Devices of this type are for example disposable equipment for a heart-lung machine, oxygenators, catheters, artificial organs such as heart or kidney, gas exchange membranes or vascular prostheses, but this list is by no means to be regarded as a conclusive list.

With these plastics surfaces it is extremely important inter alia to prevent the blood which comes into contact with the surfaces from coagulating, and overall to make the surface hemocompatible.

It is known in this connection for example to inhibit blood coagulation by giving a high dose of heparin or else to bind heparin to those surfaces coming into contact with blood.

It is further known in the state of the art to coat surfaces with hydrophilic polymers or surfactants such as, for example, Pluronic™ which, it has been possible to show, improves the hemocompatibility of surfaces which come into contact with blood. Thus, for example, U.S. Pat. No. 6,670, 199 describes various coatings which include Pluronic™ as basic structure which can be conjugated with various biomolecules.

Experiments on the applicant's premises have now shown that although the abovementioned coatings have antithrombogenic properties, they also at the same time showed a large deterioration in complement activation. The known coatings therefore do not comply in this regard with what is understood by good compatibility with blood.

Good compatibility with blood (=hemocompatibility) of a surface means specifically that on contact with blood it initiates neither blood coagulation nor the defence mechanisms of the body against the foreign surface.

The high complement activation which is surprisingly found with the known coating with Pluronic™ is precisely disadvantageous in particular because it may lead to systemic inflammations and for example cause postoperative organ failure.

Also described in the prior art are coatings with hemocompatible polymers. However, a precondition therefor is the use of suitable organic solvents. The plastics to be coated may, however, be attacked by these solvents in an unacceptable manner, thus possibly impairing the functioning of the devices. Polymers of lower molecular weight but sufficient solubility to be able to be delivered from aqueous media show a greater tendency to be washed away from the surface by the bloodstream.

SUMMARY OF THE INVENTION

Against this background, it is an object of the present invention to provide alternative substances which can be used for coating surfaces which come into contact with blood in order to improve the hemocompatibility of surfaces coated in this way, and which can be applied from aqueous media as solution or emulsion in a simple process, but nevertheless show sufficient adhesion in order not to be washed away by the blood stream.

According to one aspect of the invention, there is provided a non-ionic ester, where the nonionic ester is formed from an acyclic $C_3$-$C_6(OH)_{3-6}$ polyol and from at least three $C_{12}$-$C_{26}$ fatty acids, and where the nonionic ester further includes at least one hydrophilic group.

This is because the inventors of the present application have found that the hemocompatibility of surfaces which come into contact with blood is improved overall through the use of said nonionic esters. Compared with surfaces coated with Pluronic™, it has been possible in particular to achieve great improvements in relation to complement activation.

The inventors have for example subjected various substances which have a basic structure defined according to the invention to tests of hemocompatibility both in the HLM (heart-lung machine) in vitro test and in the Chandler loop test. With the novel coating it was possible to achieve, inter alia in the test for the number and activation of blood platelets (β-thromboglobulin), a marked improvement in the hemocompatibility compared with uncoated surfaces and surfaces coated with Pluronic™.

A further advantage over previously disclosed coatings is that an optimal adhesion of the coating to the surface which comes into contact with blood can be achieved with the newly provided substances. Good adhesion of the coating to the surface is particularly important because, on the one hand, substances which adhere inadequately may enter the bloodstream and may then possibly induce side effects in the patient. On the other hand, there is in turn the risk with coatings which adhere inadequately and are washed away by the bloodstream that the surface no longer has sufficient hemocompatibility and—besides the side effects induced by the released coating substance—there may be for example additionally activation of blood components through contact with the exposed surface.

With the coating substance which is provided for the first time herein, i.e. the nonionic ester, the at least 3 fatty acids ensure that the substance firmly adheres to the surface, or is anchored to the surface. Disadvantageous washing away with the possible consequences described above is thus successfully avoided.

In addition, the hydrophilic portion of the nonionic ester ensures the antithrombogenic property of the coating and thus its good hemocompatibility.

In a preferred embodiment, the hydrophilic group of the ester can be selected from the group comprising hydroxyl, methoxyl, ethoxyl and ethoxylate, homopolymers of vinyl compounds and copolymers of vinyl compounds. In a further refinement it is preferred for the vinyl compound to be selected from the group comprising vinylpyrrolidone, acrylamide, acrylic ester, methacrylic ester.

The inventors of the present application have realized that the hydrophilic group of the ester can be selected from the groups mentioned, because the listed groups are sufficiently hydrophilic, which is important overall for optimal hemocompatibility. As already mentioned above, the acyclic polyol forms in this case with the fatty acids an anchor via which the substance can adhere durably to the surface. The hydrophilic groups ensure the antithrombogenic effect of the coating.

In yet another refinement of the invention, the hydrophilic group is connected via the polyol to the nonionic ester.

Thus, in this embodiment, the at least one hydrophilic group is linked via the $C_3$-$C_6(OH)_{3-6}$ polyol to the ester. While at the same time ensuring the stable anchoring of the coating to the surface, in turn an adequate hydrophilic property of the coating is at the same time provided thereby.

It is preferred in another embodiment of the invention for the hydrophilic group to be connected via the fatty acid to the ester.

This embodiment also provides the advantages of a firm anchoring of the coating to the surface with, at the same time, good hydrophilic properties. In this case too, the acyclic polyol and the fatty acids provide a stable anchoring, whereas in turn the hydrophilic portion, which in this case is connected via the fatty acids to the ester, provides optimal hemocompatibility. In this embodiment for example the substance used according to the invention includes fatty acids of which at least one has an ethoxylated hydroxyl group.

It is preferred in a further embodiment for the nonionic ester to have a formula which is selected from the following formulae:

a)

$$\{H-\underset{\underset{CH_2O(CH_2CH_2O)_{c\text{-}f}-R_3}{|}}{\overset{\overset{CH_2O(CH_2CH_2O)_a-R_1}{|}}{C}}-O(CH_2CH_2O)_b-R_2\}n$$

in which
R1-3 is in each case a C12-C26 fatty acid which are identical or different, saturated or unsaturated, and which have where appropriate at least one hydroxyl group,
n is an integer from 1 to 4, and
a-f are integers which may be identical or different, where the total of the numbers a-f is between 0 and 200;

b)

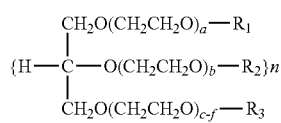

in which
R1-3 is in each case a C12-C26 fatty acid which are identical or different, and saturated or unsaturated, where at least one of the radicals$_{1-3}$ has at least one hydroxyl group,
n is an integer from 1 to 4, a-f are integers which may be identical or different, where the total of the numbers a-f is between 0 to 200;

c)

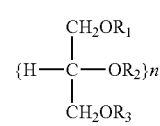

in which
R1-3 is in each case a C12-C26 fatty acid which are identical or different, and saturated or unsaturated, where at least one hydrophilic radical from homo- or copolymers of vinyl compounds is linked to at least one of the radicals R1-3,
n is an integer from 1 to 4.

It will be appreciated that, during the synthesis of the compound, the at least one hydrophilic radical will be linked to the radicals R1-3 via at least one double bond thereof.

All the alternatives mentioned provide, because of the common basic structure, the advantage that stable anchoring of the substance to the surface, and a hydrophilic property sufficient for good hemocompatibility is ensured.

The inventors have been able to show in their own experiments that a substance used according to the invention, specifically Cremophor EL which is used in the state of the art as solubilizer/emulsifier, confers an excellent hemocompatibility on the surfaces coated therewith. Cremophor represents in this connection one example of an ethoxylated nonionic ester of acyclic polyol with fatty acids. Said substance has been tested for example for the platelet count and activation (β-thromboglobulin) etc compared with substances known in the state of the art.

The inventors were able to infer from these experiments that substances of similar structure are likewise suitable for an optimal hemocompatible coating. It is preferred in a further embodiment for the nonionic ester to have a formula which is selected from the following formulae:

a)

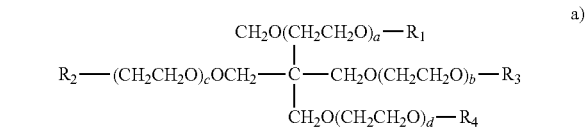

in which
R1-4 is in each case a C12-C26 fatty acid which are identical or different, saturated or unsaturated, and which have where appropriate at least one hydroxyl group, and
a-d are integers which may be identical or different, where the total of the numbers a-d is between 0 and 200;

b)

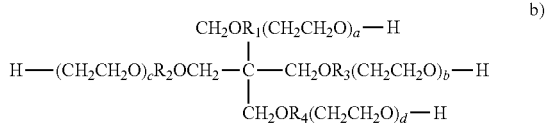

in which
R1-4 is in each case a $C_{12}$-$C_{26}$ fatty acid which are identical or different, saturated or unsaturated, where at least one of the radicals $R_{1-4}$ has at least one hydroxyl group, and a-d are integers which may be identical or different, where the total of the numbers a-d is between 0 and 200;

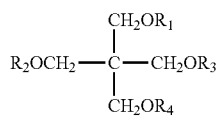

c)

in which

R1-4 is in each case a C12-C26 fatty acid which are identical or different, saturated or unsaturated, where at least one hydrophilic radical from homo- or copolymers of vinyl compounds is linked to at least one of the radicals R1-4.

It will be appreciated here too that, during the synthesis of the compound, the at least one hydrophilic radical will be linked to the radicals R1-3 via at least one double bond thereof.

With these compounds, which represent branched molecules based on pentaerythritol, it is possible to achieve a hemocompatible property of coatings which is just as good as that of the abovementioned unbranched molecules. Fatty acid esters of pentaerythritol are employed in the state of the art inter alia as emulsifiers.

In a refinement it is preferred for the nonionic ester to have an HLB (HLB=hydrophilic-lipophilic balance) of between 2 and 18, preferably between 4 and 14.

The HLB describes the ratio between hydrophilic and lipophilic portions of a chemical compound. The inventors have found that it is possible by adjusting the HLB to the stated values to provide a substance which confers on the coating an optimally adapted hydrophilic property.

It is preferred in a further embodiment for the nonionic ester to be selected from the group comprising polyoxylglycerol ricinoleate, polyoxylglycerol hydroxystearate, polyoxylsorbitol hexaoleate.

These compounds have been proved in experiments to be suitable for coating within the meaning of the present application. One example of polyoxylglycerol ricinoleate (synonym: macrogol-glycerol ricinoleate) is Cremophor® EL; one example of polyoxylglycerol hydroxystearate (synonym: macrogol-glycerol hydroxystearate) is Cremophor® WO 7, and one example of polyoxylsorbitol hexaoleate (synonym: macrogol-sorbitol hexaoleate) is Atlas® G 1086 or Atlas® G 1096. Said substances are commercially available on the market.

The enumerations are only by way of example, because it is possible to employ all conceivable substances having a structure according to the invention.

In yet another refinement it is preferred for the coating solution for the hemocompatible coating to consist of an aqueous solution or emulsion which comprises the nonionic ester.

In a further refinement it is preferred for the nonionic ester content in the aqueous solution or emulsion to be less than 2% by weight, preferably less than 0.2% by weight.

The inventors of the present application have realized that these proportions of the nonionic ester in the solution are sufficient to lead to a marked improvement in the hemocompatible properties.

Against this background, the present invention further relates to a hemocompatible coating for surfaces which come into contact with blood, in which at least one nonionic ester as defined above is applied.

It is thus possible—as already mentioned—to use the hemocompatible coating to coat surfaces of, for example, medical devices which come into contact with blood, and with which it is extremely important that they acquire good hemocompatible properties. This results in prevention of, for example, activation of the complement system in blood, or for example adsorption or activation of blood platelets or white blood corpuscles.

Against this background, the present invention further relates to a medical device having at least one surface which has the hemocompatible coating according to the invention. The surface of the medical device is preferably a plastics surface, in particular composed of polypropylene, polycarbonate, polymethylpentene, polyurethane, polyethylene, polyester, silicone, rigid or plasticized polyvinyl chloride, copolymers such as, for example, ABS, EPDM etc.

In a refinement it is preferred for the medical device to be a component of a device coming into contact with blood, preferably of disposable equipment for a heart-lung machine, an oxygenator, a catheter, an artificial heart, an artificial kidney, a gas exchange membrane or a vascular prosthesis.

It will be appreciated that the features mentioned above and yet to be explained below can be used not only in the combinations indicated in each case, but also in other combinations or alone, without departing from the scope of the present invention.

DESCRIPTION OF PREFERRED EMBODIMENTS

Further advantages are evident from the appended description and the table.

TABLE 1

Results of the Chandler loop tests

|  | Control | Uncoated | Pluronic F68 | Cremophor EL |
|---|---|---|---|---|
| Blood platelets ×10³/µl | 264 | 187 | 225 | 249 |
| β-TG IU/ml | 72.2 | 1601.0 | 1760.9 | 809.0 |
| SC5b-9 ng/ml | 156.3 | 1864.7 | 7577 | 3148 |

Table 1 shows results for test specimens with various coatings subjected to a test in the Chandler loop model. This entails tubes (loops) partly filled with blood and having various coatings being rotated in a waterbath. This results in the "blood column" and the tube rotates around the blood column and simulates a flow. After 90 minutes, blood was taken from the loops, and these samples were analyzed for certain values.

The specimens (loops) in the tests carried out in the present case consisted of 7 commercially available polycarbonate connectors which were connected by ⅜" silicone tube pieces to form a ring.

In each case 5 of such loops were assembled for the coating, and 1000 ml of aqueous coating solution was circulated using 1 m of ⅜" silicone pump tube by pumping with a tubing pump at a flow rate of two liters per minute for 20 minutes at room temperature. After the coating, the coating solution was discarded and the coated loops were, without further rinsing, blown out with sterile compressed air and thus dried. After a final drying in a drying oven at 40° C. for four hours, the coating process was complete. The coating solutions used had the following compositions: coating A: 1000 mg/liter Cremophor®EL (Caesar+Loretz GmbH, Hilden) in demineralized water; coating B: 1000 mg/liter Pluronic®F68 (AppliChem GmbH, Darmstadt) in demineralized water.

Table 1 lists the number of blood platelets after carrying out the test for each tested tube. It is evident from the table that the number of blood platelets is slightly higher with the Cremophor coating than with the Pluronic coating, but is distinctly higher than with the uncoated control.

Table 1 additionally shows the result of the β-thromboglobulin determination (quantitative, IU/ml). β-Thromboglobulin is released on activation of blood platelets, so that the β-thromboglobulin concentration is a measure of the activation of blood platelets.

As is evident from Table 1, the Cremophor coating leads to a distinctly smaller release of β-thromboglobulin than the surface coated with Pluronic™ and the uncoated surface.

Table 1 additionally shows the result of the complement SC5b-9 determination (nanograms/ml). The terminal complement complex is a relevant marker for evaluating the hemocompatibility of surfaces. SC5b-9 has the ability to attack cell membranes and, for example, to activate blood platelets. It must therefore be the aim with every coating to minimize the formation of this complement complex.

The comparison between Pluronic™ and Cremophor in Table 1 again reveals that Cremophor leads to a far lower SC5b-9 value than does Pluronic®F68 (about 3000 ng/ml for Cremophor compared with about 7600 ng/ml for Pluronic; averages in each case).

The results in the Chandler loop show that the coating according to the invention has better hemocompatible properties than the specified prior art coating.

Therefore, what is claimed, is:

1. A medical device comprising a conduit configured for transporting blood, the conduit having at least one surface intended to come into contact with the blood, the at least one surface of the conduit comprising a coating, wherein the coating comprises a nonionic ester formed from an acyclic $C_3$-$C_6(OH)_{3-6}$ polyol and from at least three C12-C26 fatty acids, where the nonionic ester further includes at least one hydrophilic group and the nonionic ester is anchored to the surface of the conduit by the at least three $C_{12}$-$C_{26}$ fatty acids so as to render the surface hemocompatible such that the coating composition is capable of adhering to the at least one surface so as to resist washing away when the coating composition is exposed to a bloodstream, wherein the nonionic ester adheres the coating directly to the surface and wherein the nonionic ester has a formula selected from the following formulae:

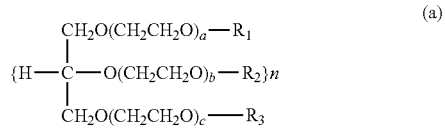
(a)

in which $R_1$, $R_2$ and $R_3$ is in each case a $C_{12}$-$C_{26}$ fatty acid which are identical or different, saturated or unsaturated, and which have where appropriate at least one hydroxyl group, n is an integer from 1 to 4, and a, b and c are integers which may be identical or different, where the total of the numbers a, b and c is between 0 and 200; and

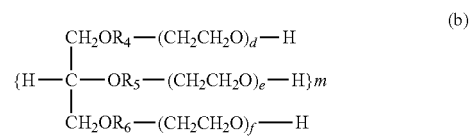
(b)

in which $R_4$, $R_5$ and $R_6$ is in each case a $C_{12}$-$C_{26}$ fatty acid which are identical or different, and saturated or unsaturated, where at least one of the radicals $R_4$, $R_5$ and $R_6$ has at least one hydroxyl group, m is an integer from 1 to 4, d, e and f are integers which may be identical or different, where the total of the numbers d, e and f is between 0 to 200.

2. The medical device of claim 1, wherein said surface of the conduit is a plastics surface and the conduit is configured to allow for the coating to be dried onto the surface of the conduit.

3. The medical device of claim 1, wherein said surface of the conduit consists of at least one of the materials polypropylene (PP), polycarbonate (PC), polymethylpentene (PMP), polyurethane (PU), polyethylene (PE), polyester, silicone, polyvinyl chloride (PVC), acrylonitrile butadiene styrene (ABS), and ethylene propylene diene monomer (EPDM).

4. The medical device of claim 1, wherein the medical device is selected from the group consisting of disposable equipment for a heart-lung machine, an oxygenator, a catheter, an artificial heart, an artificial kidney, a gas exchange membrane and a vascular prosthesis.

5. A medical device comprising a conduit configured for transporting blood, the conduit having at least one surface intended to come into contact with the blood, the at least one surface of the conduit is a plastic surface comprising a coating composition comprising a nonionic ester formed from an acyclic $C_3$-$C_6(OH)_{3-6}$ polyol and from at least three $C_{12}$-$C_{26}$ fatty acids, where the nonionic ester further comprises at least one hydrophilic group and where the nonionic ester adheres the coating directly to a portion of the medical device so as to render the portion of the medical device hemocompatible such that the coating composition is capable of adhering to the portion so as to resist washing away when the coating composition is exposed to a bloodstream, wherein the nonionic ester adheres the coating directly to the surface and wherein the nonionic ester has a formula selected from the following formulae:

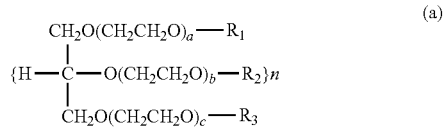
(a)

in which $R_1$, $R_2$ and $R_3$ is in each case a $C_{12}$-$C_{26}$ fatty acid which are identical or different, saturated or unsaturated, and which have where appropriate at least one hydroxyl group, n is an integer from 1 to 4, and a, b and c are integers which may be identical or different, where the total of the numbers a, b and c is between 0 and 200; and

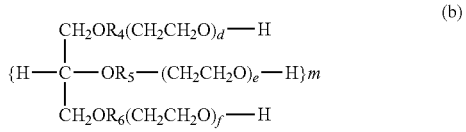

in which $R_4$, $R_5$ and $R_6$ is in each case a $C_{12}$-$C_{26}$ fatty acid which are identical or different, and saturated or unsaturated, where at least one of the radicals $R_4$, $R_5$ and $R_6$ has at least one hydroxyl group, m is an integer from 1 to 4, d, e and f are integers which may be identical or different, where the total of the numbers d, e and f is between 0 to 200, and wherein the coating composition is derived from an aqueous composition comprising the nonionic ester, wherein the content of the nonionic ester is <0.2% by weight.

6. A medical device, the medical device having at least one surface for contacting and transporting blood, at least a portion of the surface having a coating adhered thereto, the coating comprising a nonionic ester, the nonionic ester being formed from an acyclic $C_3$-$C_6(OH)_{3-6}$ polyol and from at least three $C_{12}$-$C_{26}$ fatty acids, where the nonionic ester further includes at least one hydrophilic group and adheres the coating directly to a portion of the medical device and where a sufficient amount of the nonionic ester is attached to the portion of the surface of the medical device to render the portion hemocompatible after exposure to a bloodstream for at least 90 minutes, wherein the nonionic ester has a formula selected from the following formulae:

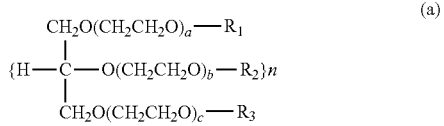

in which
$R_1$, $R_2$ and $R_3$ is in each case a $C_{12}$-$C_{26}$ fatty acid which are identical or different, saturated or unsaturated, and which have where appropriate at least one hydroxyl group,
n is an integer from 1 to 4, and
a, b and c are integers which may be identical or different, where the total of the numbers a, b and c is between 0 and 200; and

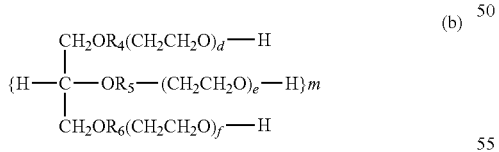

in which $R_4$, $R_5$ and $R_6$ is in each case a $C_{12}$-$C_{26}$ fatty acid which are identical or different, and saturated or unsaturated, where at least one of the radicals $R_4$, $R_5$ and $R_6$ has at least one hydroxyl group, m is an integer from 1 to 4, d, e and f are integers which may be identical or different, where the total of the numbers d, e and f is between 0 to 200.

7. The medical device of claim 1, wherein the coating composition is an aqueous composition containing the nonionic ester, wherein the content of the nonionic ester is <0.2% by weight.

8. The medical device of claim 6, wherein the coating composition is derived from an aqueous composition comprising the nonionic ester, wherein the content of the nonionic ester is <0.2% by weight.

9. The device of claim 6, wherein the nonionic ester has an HLB of between 2 and 18.

10. The device of claim 6, wherein the nonionic ester is selected from the group consisting of polyoxylglycerol ricinoleate, polyoxylglycerol hydroxystearate, and polyoxylsorbitol hexaoleate.

11. A medical device comprising a conduit configured for transporting blood, the conduit having at least one surface intended to come into contact with the blood, the at least one surface of the conduit comprising a coating, wherein the coating comprises a nonionic ester formed from an acyclic $C_3$-$C_6(OH)_{3-6}$ polyol and from at least three $C_{12}$-$C_{26}$ fatty acids, where the nonionic ester further includes at least one hydrophilic group and the nonionic ester is directly anchored to, or directly adhered to, the surface of the conduit by adsorption so as to render the surface hemocompatible such that the coating composition is capable of adhering to the portion so as to resist washing away when the coating composition is exposed to a bloodstream, and wherein the nonionic ester has a formula selected from the following formulae:

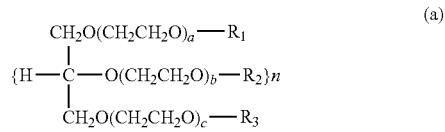

in which
$R_1$, $R_2$ and $R_3$ is in each case a $C_{12}$-$C_{26}$ fatty acid which are identical or different, saturated or unsaturated, and which have where appropriate at least one hydroxyl group,
n is an integer from 1 to 4, and
a, b and c are integers which may be identical or different, where the total of the numbers a, b and c is between 0 and 200; and

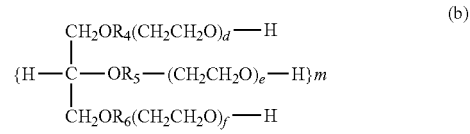

in which $R_4$, $R_5$ and $R_6$ is in each case a $C_{12}$-$C_{26}$ fatty acid which are identical or different, and saturated or unsaturated, where at least one of the radicals $R_4$, $R_5$ and $R_6$ has at least one hydroxyl group, m is an integer from 1 to 4, d, e and f are integers which may be identical or different, where the total of the numbers d, e and f is between 0 to 200.

12. The device of claim 11, where the sufficient amount of the nonionic ester is attached to the portion to render the portion hemocompatible after exposure to a bloodstream for 90 minutes.

13. The device of claim 11, wherein the nonionic ester is directly anchored to the surface of the conduit by adsorption.

14. The device of claim 11, wherein the nonionic ester is directly adhered to the surface of the conduit by adsorption.

15. A medical device having at least one surface for contacting and transporting blood, wherein at least a portion of the surface has a coating adhered thereto, wherein the coating comprises a nonionic ester that is formed from an acyclic $C_3$-$C_6(OH)_{3-6}$ polyol and from at least three $C_{12}$-$C_{26}$ fatty acids, wherein the nonionic ester further includes at least one hydrophilic group and adheres the coating directly to a portion of the medical device and a sufficient amount of the nonionic ester is attached to the portion of the surface of the medical device to render the portion hemocompatible after exposure to a bloodstream for at least 90 minutes, wherein the nonionic ester is selected from the group consisting of polyoxylglycerol ricinoleate, polyoxylglycerol hydroxystearate, and polyoxylsorbitol hexaoleate, and wherein the surface is a plastics surface.

\* \* \* \* \*